(12) United States Patent
Kim et al.

(10) Patent No.: US 12,220,551 B2
(45) Date of Patent: Feb. 11, 2025

(54) TATTOO NEEDLE UNIT (71) Applicant: Miartek, Seongnam-si (KR)

(72) Inventors: Sang Rae Kim, Seoul (KR); Hyun Sook Jin, Seoul (KR)

(73) Assignee: Miartek, Seongnam-si (KR)

( * ) Notice: Subject to any disclaimer, the term of this patent is extended or adjusted under 35 U.S.C. 154(b) by 317 days.

(21) Appl. No.: 17/334,835

(22) Filed: May 31, 2021

(65) Prior Publication Data
US 2021/0386988 A1    Dec. 16, 2021

(30) Foreign Application Priority Data

Jun. 12, 2020  (KR) .................. 10-2020-0071557
Nov. 27, 2020  (KR) .................. 10-2020-0162778

(51) Int. Cl.
*A61M 37/00*    (2006.01)
(52) U.S. Cl.
CPC .............................. *A61M 37/0076* (2013.01)
(58) Field of Classification Search
CPC ........ A61M 37/0076–0084; A01K 11/00–008; A61Q 1/00–145
See application file for complete search history.

(56) References Cited

U.S. PATENT DOCUMENTS

| 9,636,491 | B1* | 5/2017 | O'Brien, III | ...... A61M 37/0015 |
| 2004/0116953 | A1* | 6/2004 | Dixon | ............... A61M 37/0076 606/186 |
| 2006/0021890 | A1* | 2/2006 | Wang | ............... A61M 37/0076 206/363 |
| 2014/0343591 | A1* | 11/2014 | Alul | ....................... A61M 5/46 606/186 |

FOREIGN PATENT DOCUMENTS

| KR | 101691208 B1 * | 12/2016 | ........ A61M 37/0076 |
| KR | 102031702 B1 * | 4/2019 | ........ A61M 37/0076 |

* cited by examiner

*Primary Examiner* — Brigid K Byrd
(74) *Attorney, Agent, or Firm* — Park, Kim & Suh, LLC

(57) ABSTRACT

Tattoo needle unit according to the present invention includes a pocket having a body part; at least one first needle having a first diameter and coupled to the pocket; and at least one second needle having a second diameter larger than the first diameter and coupled to the pocket, wherein, a part of the first needle is exposed out of the body part, and another part of the first needle is disposed inside the body part, and wherein, a part of the second needle is exposed out of the body part, and another part of the second needle is disposed inside the body part. According to the tattoo needle unit according to the present invention, there is an advantage in that it is possible to easily implement a tattoo of a more diverse and natural shape due to the combination of various types of needles.

17 Claims, 14 Drawing Sheets

TATTOO NEEDLE UNIT

CROSS-REFERENCE TO RELATED APPLICATIONS

A claim for priority under 35 U.S.C. § 119 is made to Korean Patent Application No. 10-2020-0071557 filed on Jun. 12, 2020 and Korean Patent Application No. 10-2020-0162778 filed on Nov. 27, 2020, in the Korean Intellectual Property Office, the entire contents of which are hereby incorporated by reference.

TECHNICAL FIELD

The present invention relates to a tattoo needle unit that makes it possible to easily create various and natural tattoos.

BACKGROUND ART

Tattoos are used to inject fine prints or patterns by injecting pigment while creating a fine scratch on the skin.

A cartridge-type needle unit is mainly used for tattooing, and the conventional cartridge-type tattoo needle unit is formed in a form in which a plurality of needles are arranged in a pocket.

Here, it is generally configured such that the outline formed by the tip of each needle forms an oblique line by combining needles having different lengths, and the thickness of the needles is the same, and the space between the needles is densely arranged.

However, as described above, in a conventional tattoo needle unit, needles of the same thickness are combined, and since the spacing between the needles is very close, it is difficult to accurately use various tattoo techniques. As a result, there is a problem in that it is difficult to implement various and natural tattoos in a desired shape.

TECHNICAL PROBLEM TO BE SOLVED

The present invention has been conceived to solve the problems of the prior art described above, and is to provide a tattoo needle unit capable of easily implementing various types of tattoos.

DETAILED DESCRIPTION OF THE INVENTION

Technical Solution

Tattoo needle unit according to the present invention includes a pocket having a body part; at least one first needle having a first diameter and coupled to the pocket; and at least one second needle having a second diameter larger than the first diameter and coupled to the pocket, wherein, a part of the first needle is exposed out of the body part, and another part of the first needle is disposed inside the body part, and wherein, a part of the second needle is exposed out of the body part, and another part of the second needle is disposed inside the body part.

In the tattoo needle unit according to the present invention, the first needle and the second needle are arranged on the body part in a row in a longitudinal direction of the body part and neighboring needles are spaced with a predetermined distance.

Tattoo needle unit according to the present invention may include one first needle and one second needle.

Tattoo needle unit according to the present invention may include two first needles and one second needle.

Tattoo needle unit according to the present invention may include one first needle and two second needles.

Tattoo needle unit according to the present invention may include one first needles and three second needle.

In the tattoo needle unit according to the present invention, the predetermined distance may be 1 to 2 mm.

In the tattoo needle unit according to the present invention, the pocket may further include at least one wing part protruding from the body part in a direction which is perpendicular to the longitudinal direction of the body part.

In the tattoo needle unit according to the present invention, the pocket may include two wing parts protruding to the opposite direction each other.

In the tattoo needle unit according to the present invention, the second needle may have a structure in which a plurality of fine needles are densely arranged to form a combination and the second diameter is a diameter of a circumference extending along the maximum diameter of the outer circumference of the fine needle combination.

In the tattoo needle unit according to the present invention, the second needle may be the combination of three fine needles.

Tattoo needle unit according to another embodiment of the present invention may include a pocket having a body part, at least two needles coupled to the body part and arranged on the body part in a first row in a longitudinal direction of the body part, and at least two needles coupled to the pocket and arranged on the body in a second row in the longitudinal direction of the body part, each needles in the second row are arranged next to each needles in the first row, at least front end parts of the needles are exposed to the outside of the body part and some parts of the needles are disposed inside the body part, wherein, the needles in the first row and the needles in the second row are arranged alternately each other, wherein, each needles of the first row and each needles of the second row arranged next to each needles of the first row are overlapped by 25 to 75% of their diameter in a direction which is perpendicular to the longitudinal direction of the body part.

In the tattoo needle unit according to another embodiment of the present invention, each needles of the first row and each needles of the second row arranged next to each needles of the first row may be overlapped by 50% of their diameter in a direction which is perpendicular to the longitudinal direction of the body part of the pocket.

Tattoo needle unit according to another embodiment of the present invention, two needles may be arranged in the first row and two needles are arranged in the second row.

Tattoo needle unit according to another embodiment of the present invention, the pocket may further include at least one wing part protruding from the body part in a direction which is perpendicular to the longitudinal direction of the body part.

Tattoo needle unit according to another embodiment of the present invention, the pocket may include two wing parts protruding to the opposite direction each other.

Tattoo needle unit according to another embodiment of the present invention, each needles may have a structure in which a plurality of fine needles are densely arranged to form a combination and the diameter of each needles is a diameter of a circumference extending along the maximum diameter of the outer circumference of the fine needle combination.

Tattoo needle unit according to another embodiment of the present invention, each needles may be combination of three fine needles.

A tattoo system according to the present invention may includes a tattoo needle unit including a body part accommodating a plurality of needles, and at least one wing part protruding from the body part, and a tattoo device. Here, the tattoo needle unit is designed to be mounted on the tattoo device. The tattoo device may include a body including a hollow penetrating in the longitudinal direction; a compressing ring coupled to the front end of the body; a chuck disposed inside the compressing ring to grip the body part of the tattoo needle unit according to the state of protrusion from the compression ring, the chuck including a plurality of elastic support parts and a plurality of pressing parts extending from each elastic support part and protruding outside the compression ring; a push member including a shaft portion disposed inside the body and coupled to the elastic support portion, and a button portion protruding in the rear end direction of the body; and a spring disposed between the shaft part and the body and providing elastic force to the push member.

Advantageous Effects

According to the tattoo needle unit according to the present invention, there is an advantage in that it is possible to easily implement a tattoo of a more diverse and natural shape due to the combination of various types of needles.

TECHNICAL SUBJECT

Best Mode

Hereinafter, each embodiment of the present invention will be described in detail with reference to FIGS. 1 to 14.

1) The First Embodiment (Referencing to FIGS. 1 to 8)

The tattoo needle unit 10 according to the first embodiment includes a first needle 11 having a first diameter D1 and a second needle 12 having a second diameter D2 greater than the first diameter D1. The second needle 12 has a structure in which a plurality of fine needles 121 are densely arranged to form a combination. The second diameter D2 means a diameter of a circumference extending along the maximum diameter of the outer circumference of the fine needle combination.

Here, the first diameter (D1) of the first needle 11 may be 0.3 to 0.45 mm, the second diameter (D2) of the second needle 12 may be 0.4 to 0.7 mm.

The first diameter D1 may be 0.4 to 0.45 mm, and the second diameter D2 may be 0.5 to 0.7 mm.

The tattoo needle unit 10 according to the first embodiment may be composed of A-type, B-type, C type, and D-type as follows according to the number and arrangement of the needles 11 and 12.

In the A-type, one first needle 11 and one second needle 12 are provided. (see FIGS. 1 and 2)

In the B-type, two first needles 11 and one second needle 12 are provided. The second needle 12 is provided between the two first needles 11. See FIGS. 3 and 4.

In the C type, one first needle 11 is provided and two second needles 12 are provided. The first needle 11 is provided between the two second needles 12. See FIGS. 5 and 6.

In the D type, a plurality of second needles 12 and at least one first needle 11 are provided. The plurality of second needles 12 may be arranged side by side each other and the at least one first needle 11 may be provided next to the second needles 12. For example, three second needles 12 may be arranged side by side and one first needle 11 may be arranged next to the three second needles 12. See FIGS. 7 and 8.

Commonly in the every types, a part (tip part) of each of the needles 11 and 12 is exposed to the outside of the pocket 20, and the other part (the middle part) is inserted into the pocket 20. Each of the needles 11 and 12 is arranged in a row side by side, and the distance between the needles 11 and 12 is 1 to 2 mm.

Hereinafter, the function of each type of tattoo needle unit will be described.

Figure 1:
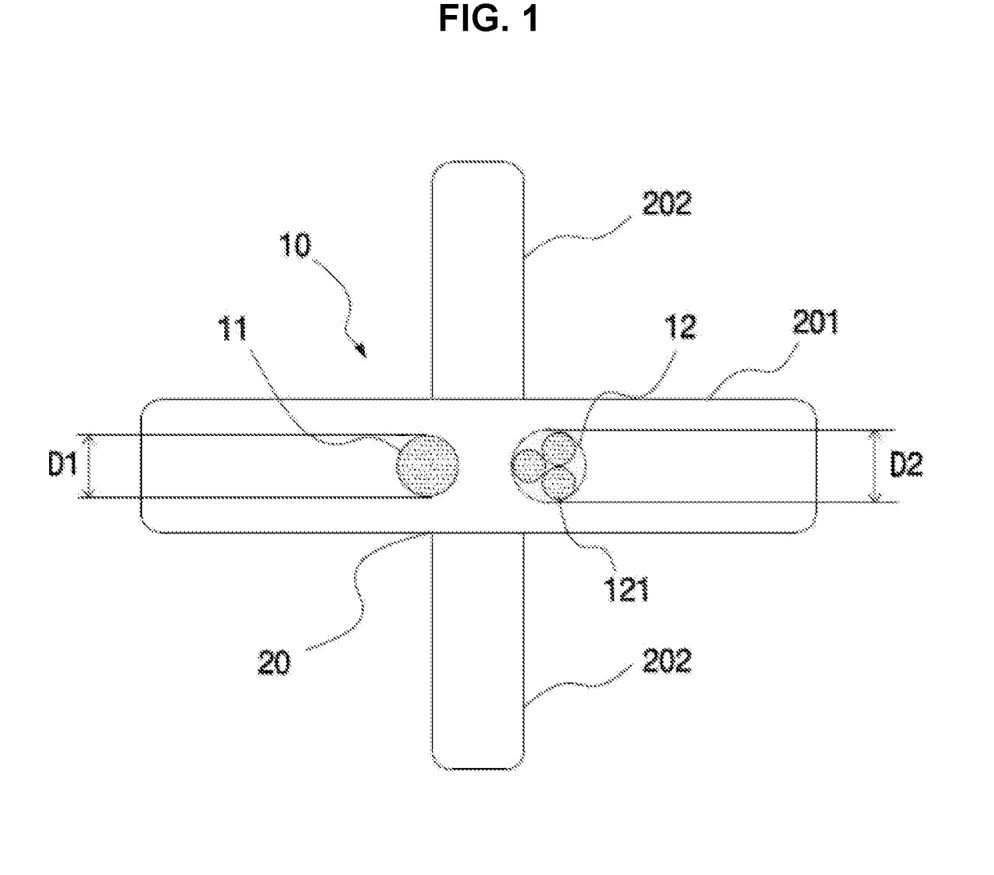
FIG. 1 is a plan view showing the A-type tattoo needle unit according to the first embodiment of the present invention.
Figure 2:
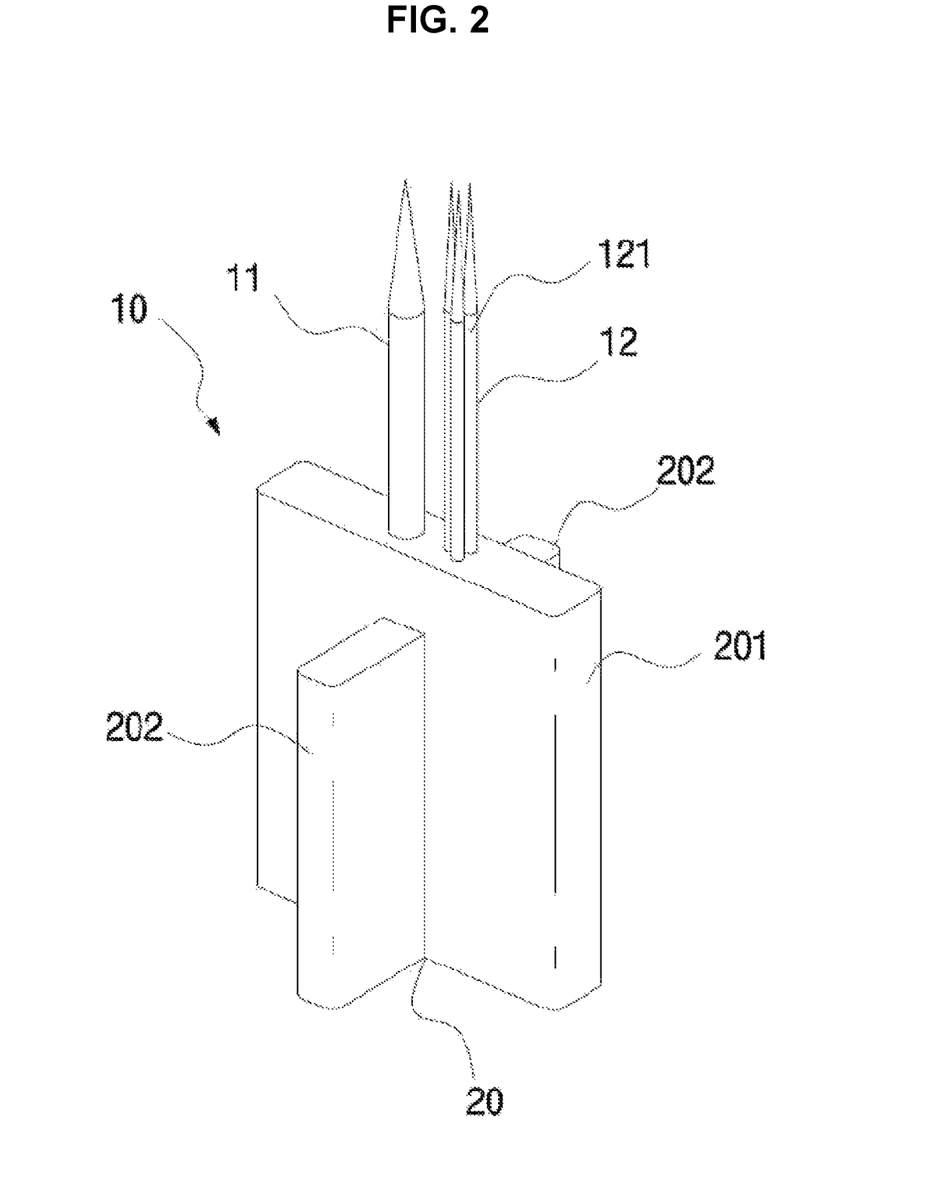
FIG. 2 is a perspective view showing a A-type tattoo needle unit according to a first embodiment of the present invention

First, according to the type A, the first needle 11 and the second needle 12 are used at the same time to express lines of different thickness at the same time, thereby enabling rapid work.

Because depending on the angle, not only the spacing between the two drawn lines varies, but also selectively expressing only a thin line using only the first needle 11, or only a thick line in which fine lines are combined using only the second needle 12 is available, it is possible to express various expressions.

For example, if the distance between the two lines is wider, the sparce eyebrow is expressed, and if the distance between the two lines is narrowed, the dense eyebrow is expressed.

Figure 3:
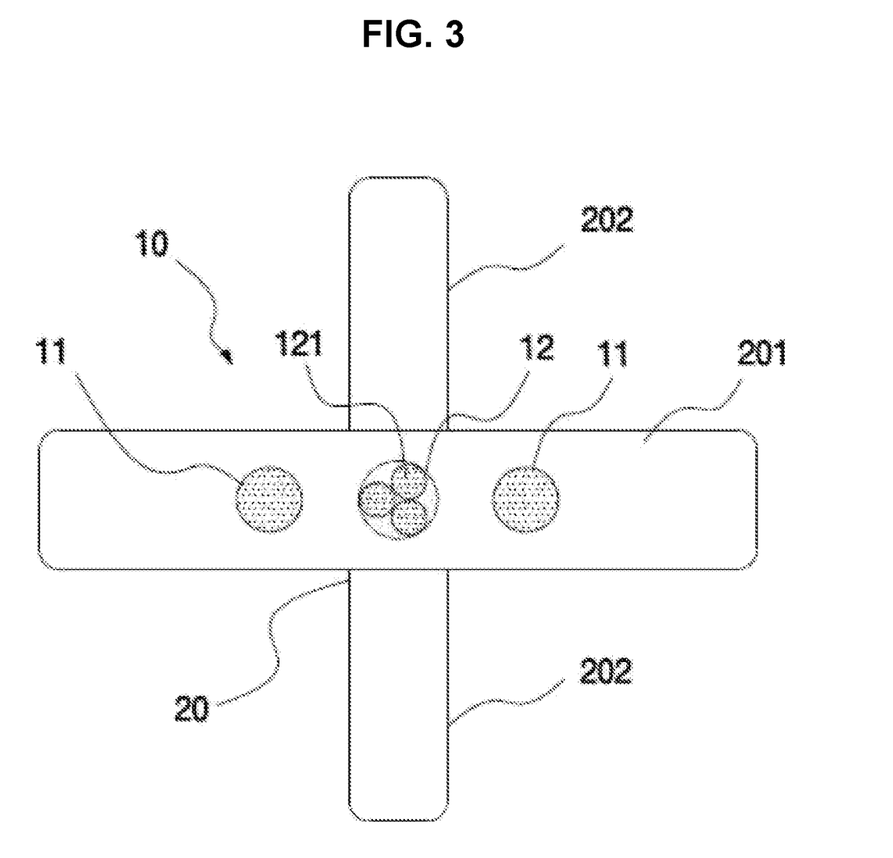
FIG. 3 is a plan view showing the B-type tattoo needle unit according to the first embodiment of the present invention.
Figure 4:
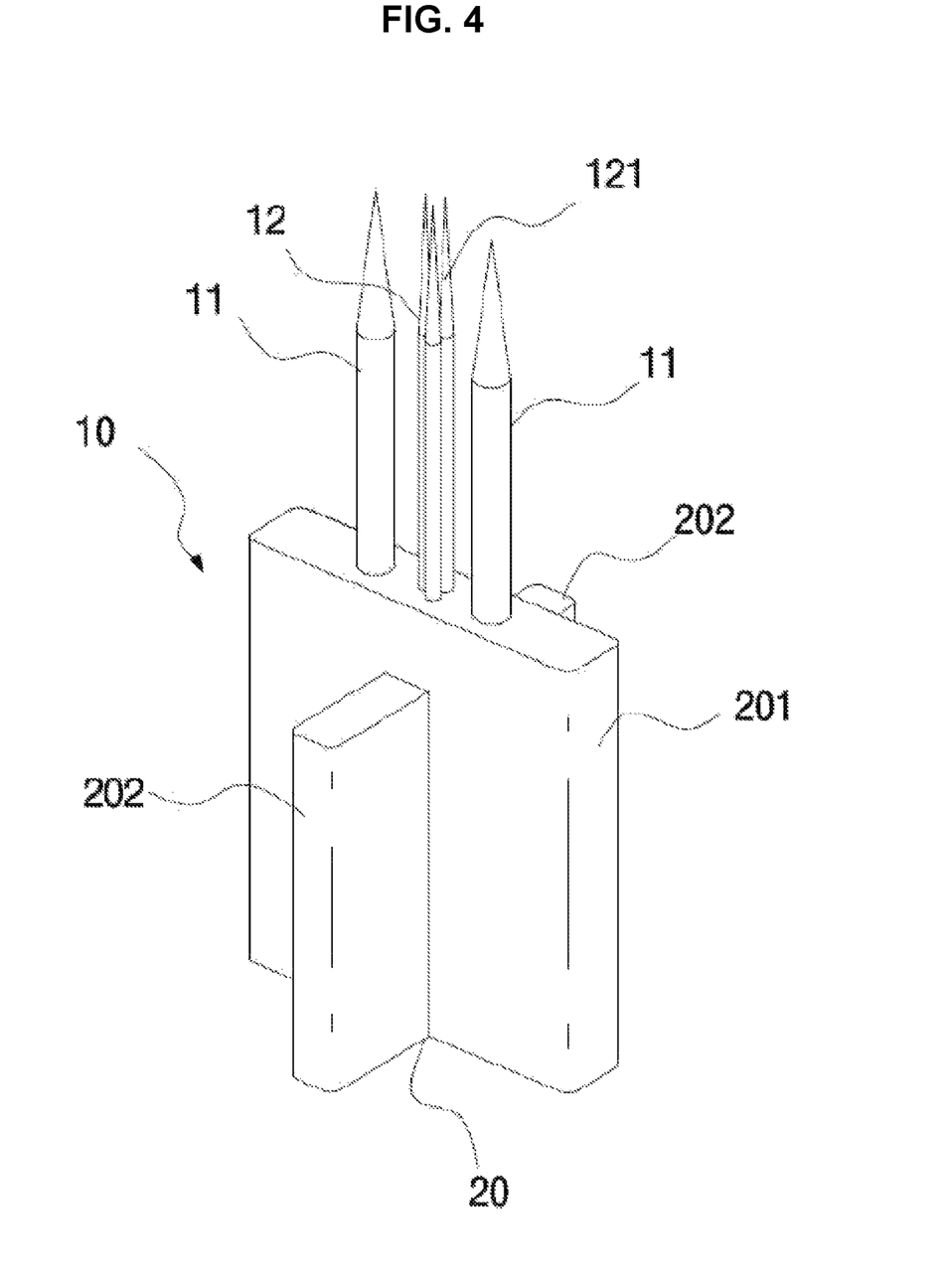
FIG. 4 is a perspective view showing B-type tattoo needle unit according to the first embodiment of the present invention.

Using the B-type, a thick line combined with fine lines can be expressed by the second needle 12 arranged in the center, and a thin line can be expressed by the first needles 11 on both sides. By doing so, it is possible to express lines that provide a sense of stability. Also, it is easy to perform a so-called curve procedure in which lines are rotated with the second needle 12 as a central axis during treatment of the fore of the eyebrow.

In addition, it is easy to freely adjust the spacing and depth of the lines according to the angle of inclination, and since the number of needles 11 and 12 is three, it is possible to express three lines at the same time, enabling rapid treatment.

If necessary, it is possible to express only a thick line in which fine lines are combined by the second needle 12 by giving an inclination, or only a thin line by the first needle 11.

In particular, when performing hair treatment, it is possible to express the relatively thin hair part of the front part of the head more naturally.

Figure 5:
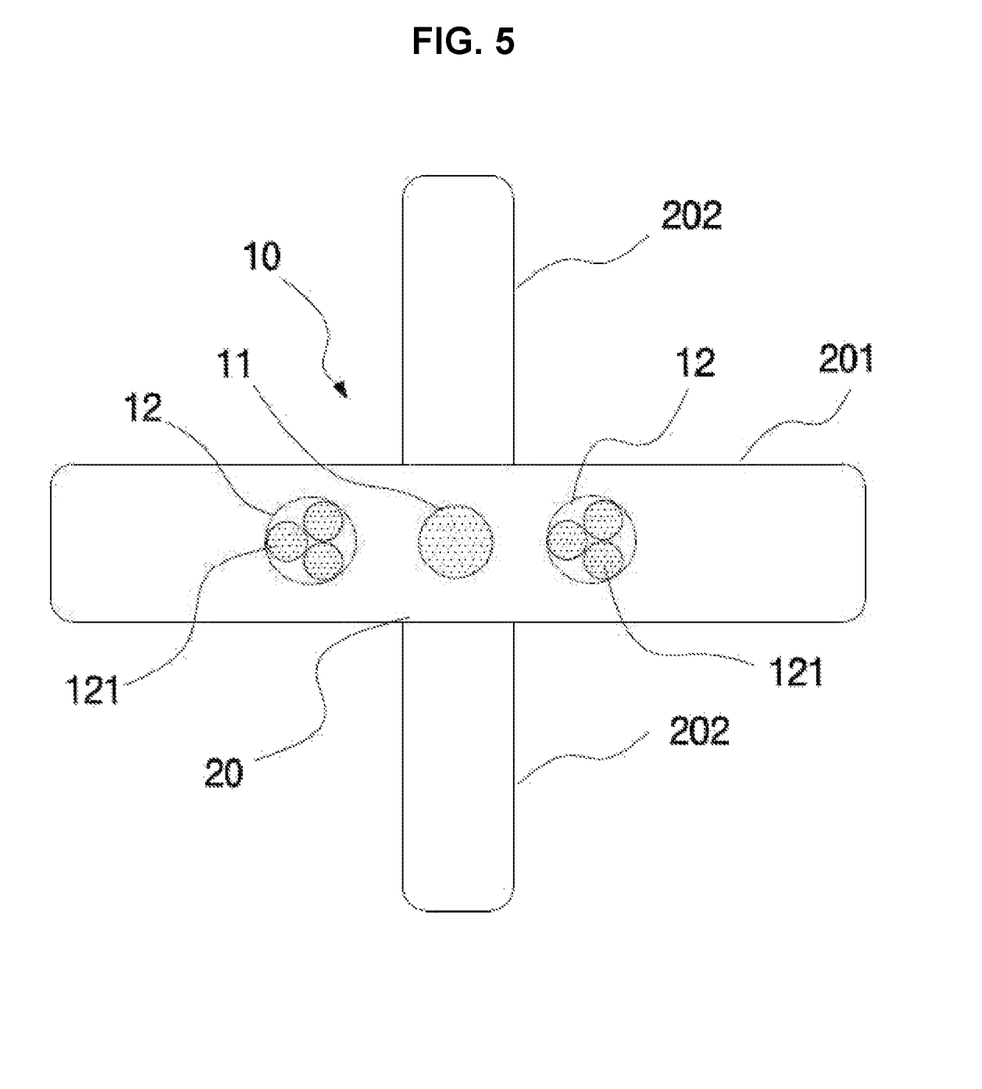
FIG. 5 is a plan view showing C-type tattoo needle unit according to the first embodiment of the present invention.
Figure 6:
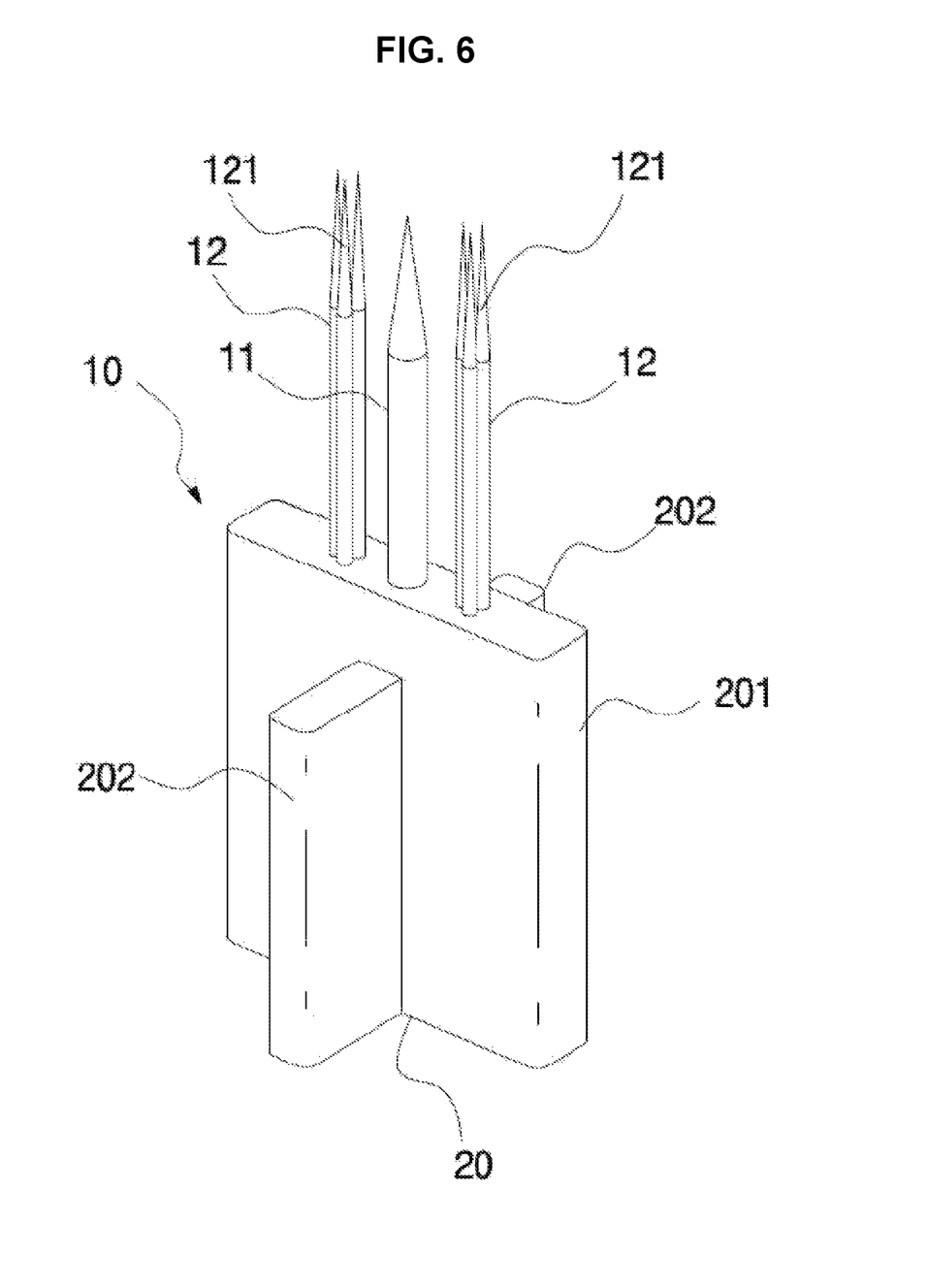
FIG. 6 is a perspective view showing the C-type tattoo needle unit according to the first embodiment of the present invention.

And by using the C type, various expression techniques are possible in a manner opposite to that of the B-type.

Figure 7:
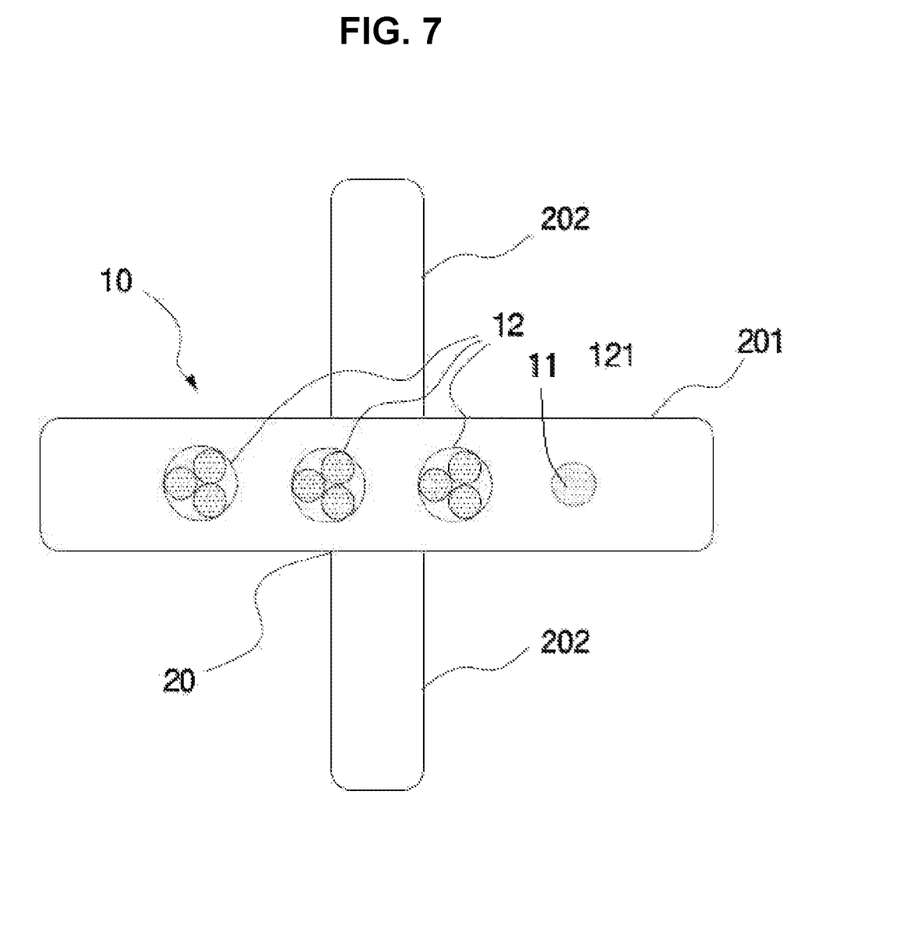
FIG. 7 is a plan view showing the D-type tattoo needle unit according to the first embodiment of the present invention.
Figure 8:
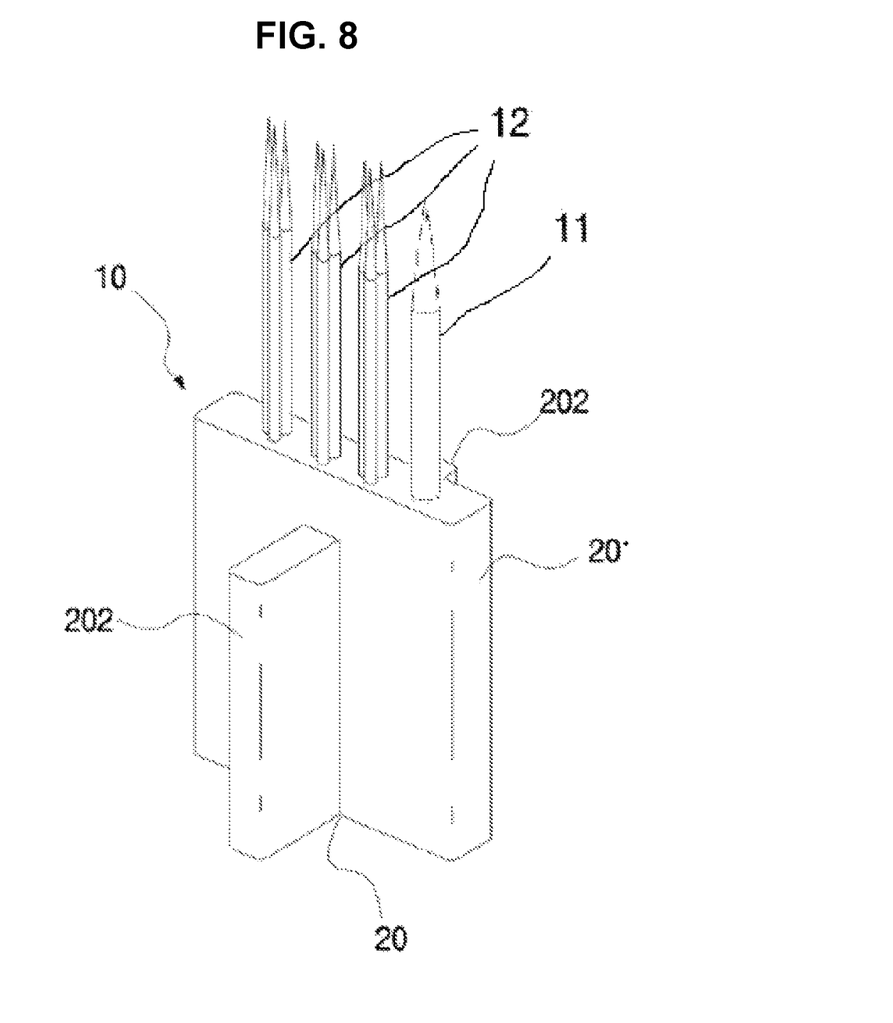
FIG. 8 is a perspective view showing the D-type tattoo needle unit according to the first embodiment of the present invention.

Type D is specialized for hairline treatment. Since the D-type has a structure in which a plurality of second needles 12 are arranged at regular intervals, the treatment is performed as if combing the hair with a hairbrush, and it is possible to delicately express a line of hair that is like real hair.

Specifically, detailed expression is possible with the embossing technique for dense areas of hair, delicate expression is possible for areas with thin hair such as the forehead and temples, and pointillism technique is possible for areas such as the crown.

In addition, due to the feature of the plurality of second needles 12 arranged side by side, it is possible to freely adjust the spacing between each line according to the angle at which the line is drawn, or by varying the number of needles 12 in contact with the skin, thereby enabling to express the sparse or dense hairs effectively.

2) The Second Embodiment (See FIGS. 9 to 12)

The tattoo needle unit 10' according to the second embodiment includes two first rows of needles 13 arranged side by side and two second rows of needles 13 arranged side by side next to the first row of needles 13. (See FIGS. 9 and 10.)

The needles 13 of the first row and the needles 13 of the second row of needles 13 are arranged alternately one by one, and the needle 13 of the first row and the needle 13 of the second row are overlapped by 25 to 75% of their diameter in a direction which is perpendicular to the longitudinal direction of the body part 201 of the pocket 20, which will be described. (See FIG. 11).

The needle 13 of the first row and the needle 13 of the second row may be overlapped by 50% of their diameter in a direction which is perpendicular to the longitudinal direction of the body part 201 of the pocket 20. (See FIG. 12.)

Figure 11:
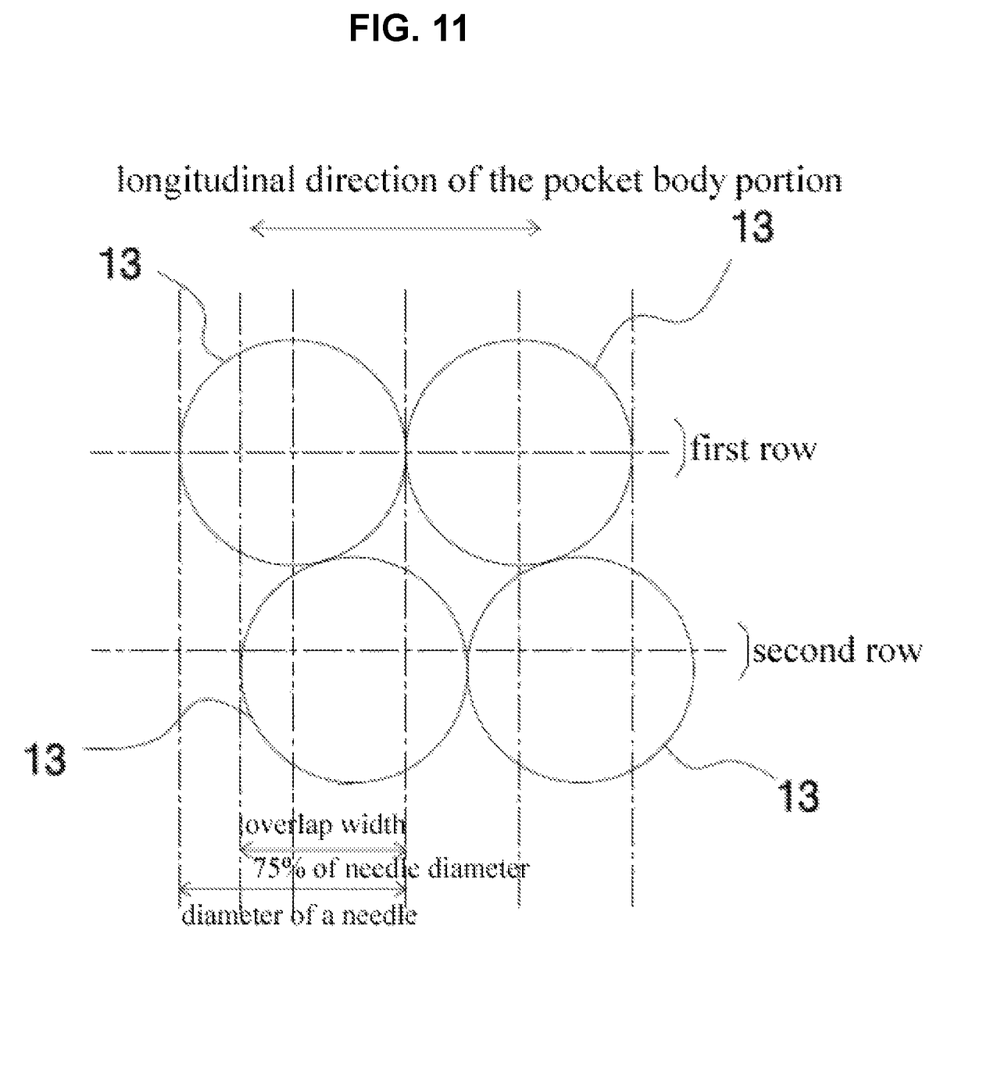
FIG. 11 is a view showing an overlapping structure of the needles according to the second embodiment of the present invention.
Figure 12:
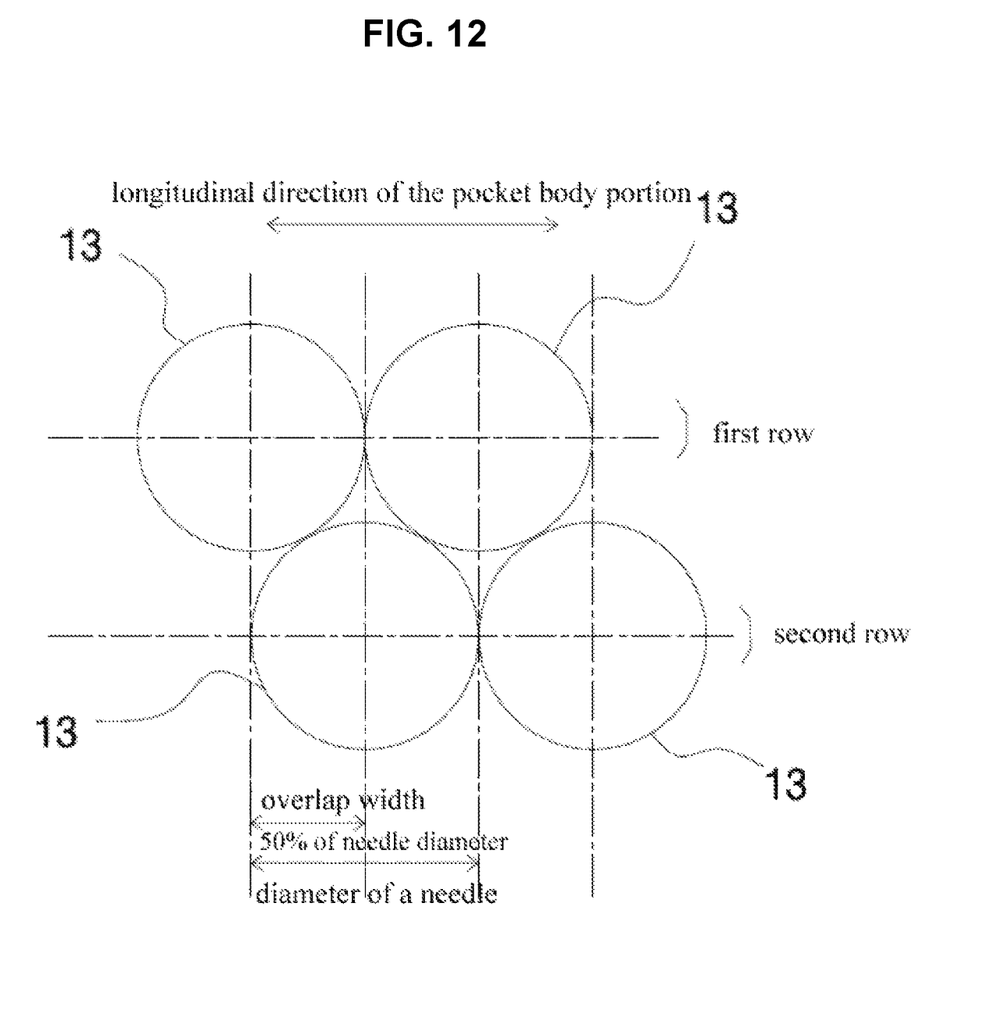
FIG. 12 is a view showing another overlapping structure of the needles according to the second embodiment of the present invention.

The needles 13 in the first row and the needles 13 in the second row may be in contact with each other. Three of the needles 13 in the first row and the second row may contact each other.

Figure 9:
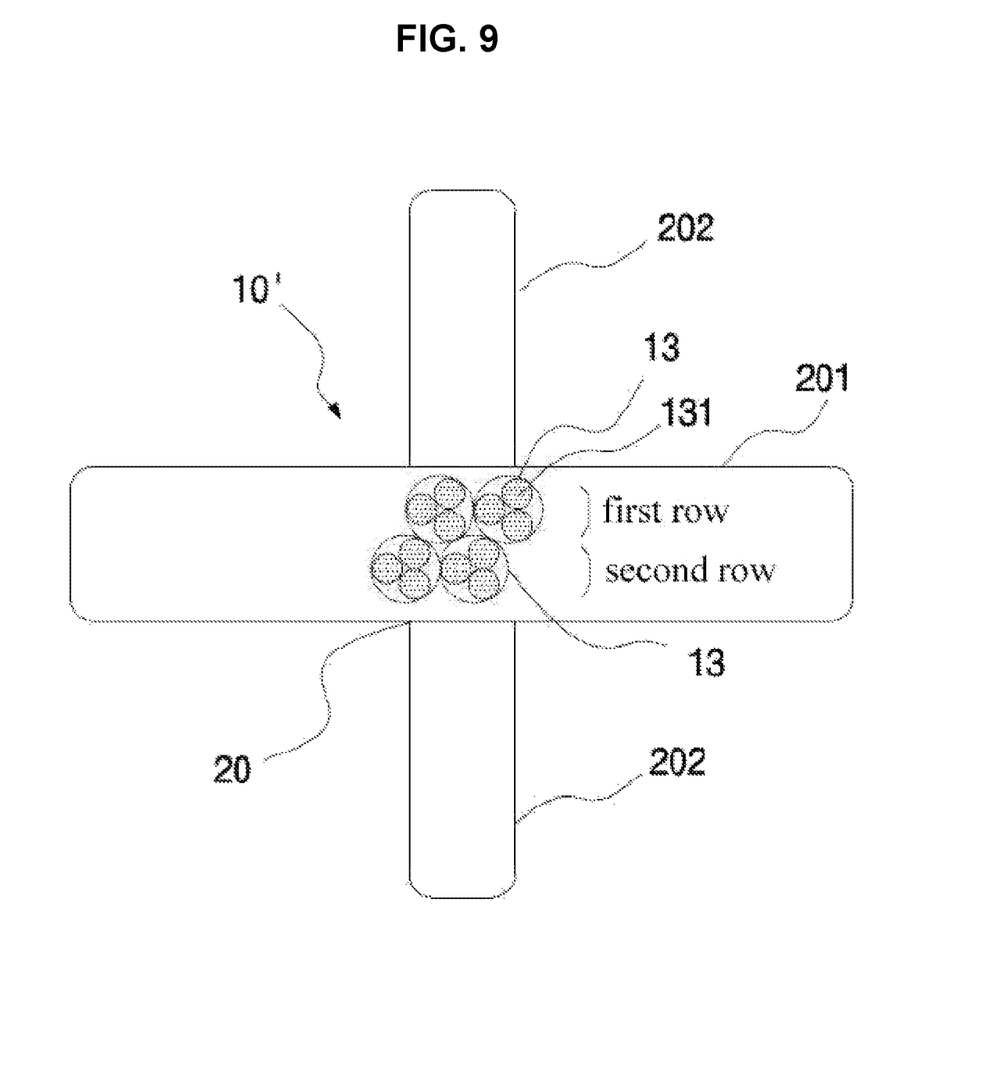
FIG. 9 is a plan view showing the tattoo needle unit according to the second embodiment of the present invention.
Figure 10:
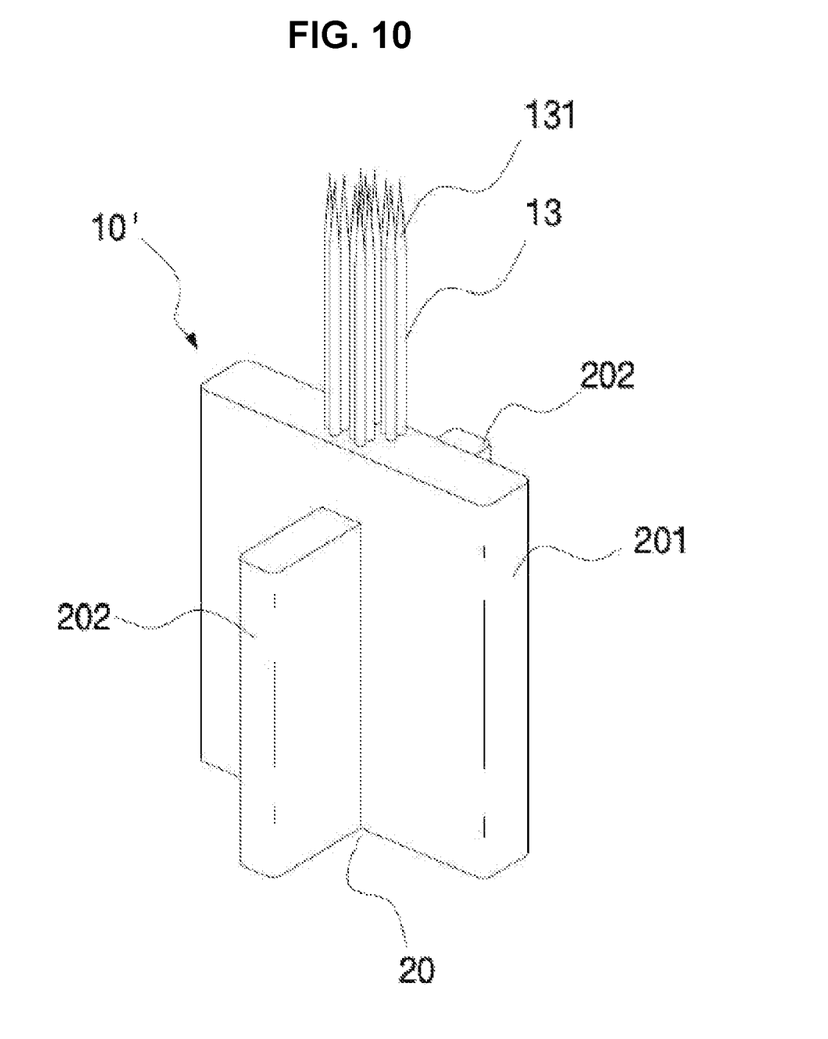
FIG. 10 is a perspective view showing a tattoo needle unit according to the second embodiment of the present invention.

Portions (tip parts) of the needles 13 of first row and portions(tip parts) of the needles 13 of the second row may be exposed to the outside of the pocket 20 and the other parts (middle part) may be inserted into the pocket 30.

Here, each of the needles 13 may have a structure in which a plurality of fine needles 131 are densely arranged to form a combination, similar to the second needle 12 of the first embodiment.

The function of the tattoo needle unit 10' according to the second embodiment will be described hereinafter.

First, since the skin around the eye where the eye line is treated is a very sensitive mucous membrane, it is desirable to be treated with minimal touch. The tattoo needle unit 10' according to the second embodiment is specialized for so-called eyeline procedures. In the tattoo needle unit 10' according to the second embodiment, since the needles 13 in the first row and the needles 13 in the second row are alternately arranged, the feeling of contacting the skin during the procedure is somewhat dull, the pain the person undergoing the treatment can be reduced.

In addition, since each needles 13 are closely arranged as a whole, the distance between the line and the line is closely expressed, a rapid procedure is possible, and side effects such as bleeding and pain can be reduced to a minimum.

The pocket 20 according to the each embodiment as described above includes a body part 201 in which needles are disposed and at least one wing part 202 protruding laterally from the body part 201.

Here, the wing parts 202 may be formed to be symmetrical to each other with reference to the body part 201, so that the cross section of the pocket 20 may be formed in a cross shape. Therefore, it can be structurally stably gripped on the chuck 60 of the tattoo device 6 described later.

In addition, the top surface of the wing part 202 may be made at a lower height than the top surface of the body part 201 or the same height. In the case of a lower height, since the wing part 202 is not in contact with the skin, the stability of the work can be increased.

Figure 13:
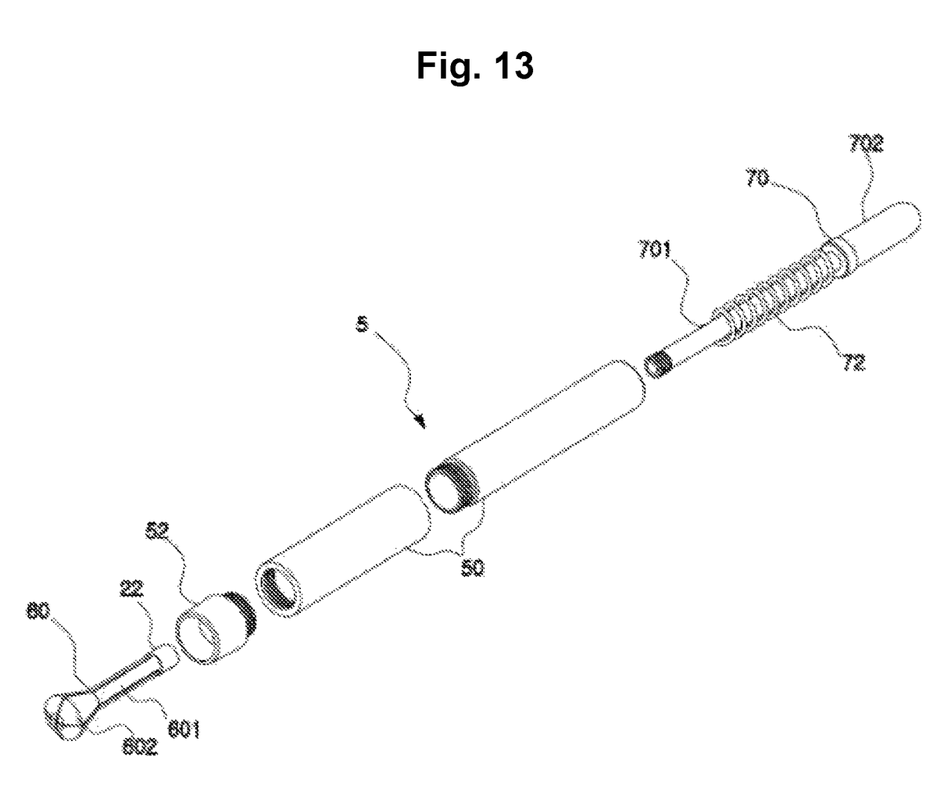
FIG. 13 is an exploded view showing a tattoo device equipped with a tattoo needle unit according to the present invention.
Figure 14:
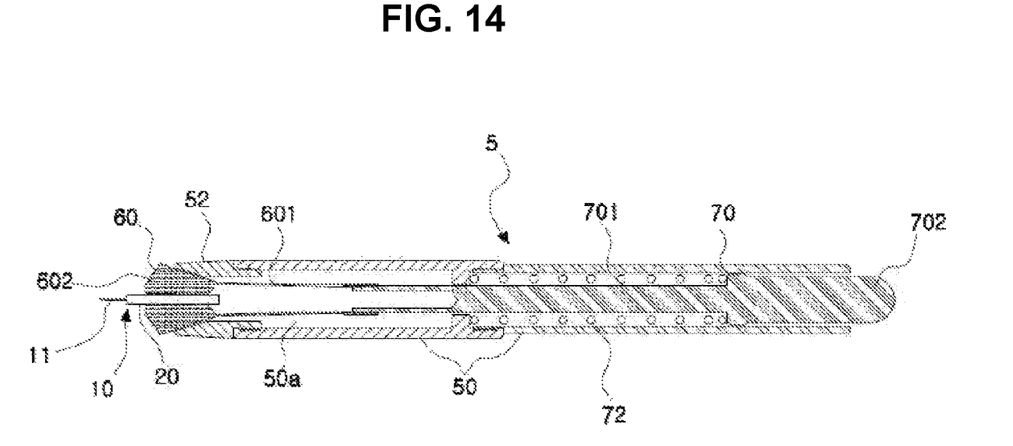
FIG. 14 is a view showing a state in which the tattoo needle unit according to the present invention is mounted on a tattoo device.

The tattoo needle unit according to the embodiments as described above may be mounted on the tattoo device 5 as shown in FIGS. 13 and 14, and used as a tattoo system.

The tattoo device 5 may include a body 50 including a hollow 50a penetrating in the longitudinal direction; a compression ring 52 coupled to the front end of the body 50; a chuck 60 disposed inside the body 50 to grip the pocket 20 of the tattoo needle unit 10 according to the state of protrusion from the compression ring 52; a push member 70 providing an operating pressure to the chuck 60 in the front end direction of the body 50; a spring 72 providing elastic force to the push member 70.

The chuck 60 may include a plurality of elastic support parts 601 and a plurality of pressing parts 602 extending from each elastic support part 601 and protruding outside the compression ring 52.

The push member 70 may include a shaft portion 701 disposed inside the body 50 and coupled to the elastic support portion 601; and a button portion 702 protruding in the rear end direction of the body 50. The spring 72 is fitted to the shaft part 701.

REFERENCE SIGNS AND NUMERALS

10: Tattoo needle unit
11: The first needle

12: The second needle
10': Tattoo needle unit
13: needle
20: pocket
201: body part
202: wing part

What is claimed is:

1. A tattoo needle unit including:
   a pocket having a body part having a first rectangular shape extended in a horizontal direction;
   a first needle having a first diameter and coupled to the pocket; and
   a first combination of three fine needles that are in contact with each other and coupled to the body part, wherein a second diameter of a first outer Soddy circle of the first combination of three fine needles is greater than the first diameter and a third diameter of each of the first combination of three fine needles that are in contact with each other is less than the first diameter,
   wherein a height of the first needle is substantially equal to a height of the first combination of three fine needles,
   wherein the first needle is spaced apart from the first combination of three fine needles with a predetermined distance,
   wherein, a part of the first needle is exposed out of the body part, and another part of the first needle is disposed inside the body part, and
   wherein, a part of the first combination of three fine needles is exposed out of the body part, and another part of the first combination of three fine needles is disposed inside the body part.

2. The tattoo needle unit of claim 1, wherein, the first needle and the first combination of three fine needles are arranged on the body part in a horizontal row.

3. The tattoo needle unit of claim 2, further comprising a second needle.

4. The tattoo needle unit of claim 2, further comprising a second combination of three fine needles that are in contact with each other.

5. The tattoo needle unit of claim 2, further comprising:
   a second combination of three fine needles that are in contact with each other; and
   a third combination of three fine needles that are in contact with each other.

6. The tattoo needle unit of claim 2, wherein, the predetermined distance is 1 to 2 mm.

7. The tattoo needle unit of claim 2, wherein the pocket further includes at least one wing part protruding from a center portion of the body part in a vertical direction.

8. The tattoo needle unit of claim 7, wherein the pocket includes two of the at least one wing part protruding in opposite directions from each other.

9. The tattoo needle unit of claim 1, wherein the pocket further includes upper and lower wing parts having a second rectangular shape extended from a center of the body part in a vertical direction such that cross sections of the body part and the upper and lower wing parts form a cross shape.

10. A tattoo needle unit including:
    a pocket having a body part extended in a horizontal direction,
    first and second combinations of three fine needles that are in contact with each other, the first and second combinations of three fine needles being coupled to the body part, wherein a first outer Soddy circle of the first combination of three fine needles and a second outer Soddy circle of the second combination of three fine needles are arranged on the body part in a first horizontal row, and
    third and fourth combinations of three fine needles that are in contact with each other, the third and fourth combinations of three fine needles being coupled to the body part, wherein a third outer Soddy circle of the third combination of three fine needles and a fourth outer Soddy circle of the fourth combination of three fine needles are arranged on the body part in a second horizontal row which is lower than the first horizontal row,
    at least front end parts of the first, second, third, and fourth combinations of three fine needles are exposed to the outside of the body part and some parts of the first, second, third, and fourth combinations of three fine needles are disposed inside the body part,
    wherein, the first and second combinations of three fine needles in the first horizontal row and the third and fourth combinations of three fine needles in the second horizontal row are arranged alternately with each other,
    wherein the first outer Soddy circle of the first combination of three fine needles is vertically overlapped with the third outer Soddy circle of the third combination of three fine needles by 25 to 75% of a diameter of the first outer Soddy circle.

11. The tattoo needle unit of claim 10, wherein the first outer Soddy circle is vertically overlapped with the third outer Soddy circle by 50% of the diameter of the first outer Soddy circle.

12. The tattoo needle unit of claim 10, wherein the pocket further includes at least one wing part protruding from a center portion of the body part in a vertical direction.

13. A tattoo system including:
    a tattoo needle unit including a body part accommodating a plurality of needles, and upper and lower wing parts protruding from the body part, wherein the body part has a first rectangular shape extended in a horizontal direction and the upper and lower wing parts have a second rectangular shape extended from a center of the body part in a vertical direction such that cross sections of the body part and the upper and lower wing parts form a cross shape; and
    a tattoo device,
    wherein the tattoo needle unit is designed to be mounted on the tattoo device,
    wherein the tattoo device includes:
      a body including a hollow penetrating in a longitudinal direction of the body;
      a compression ring coupled to a front end of the body;
      a chuck disposed inside the compression ring, the chuck being configured to grip the body part of the tattoo needle unit according to the state of protrusion from the compression ring, the chuck including a plurality of elastic support parts and a plurality of pressing parts extending from each of the plurality of elastic support parts and protruding outside the compression ring;
      a push member including a shaft portion disposed inside the body and coupled to the plurality of elastic support parts, and a button portion protruding in a rear end direction of the body; and
      a spring disposed between the shaft portion and the body and providing elastic force to the push member;
    wherein the tattoo needle unit further comprises:
      a first needle having a first diameter and coupled to the body part; and a first combination of three fine needles that are in contact with each other and coupled to the body part, wherein a second diameter of a first outer Soddy circle of the first combination of three fine needles is greater than the first diameter and a third diameter of each of the first combination of three fine needles is less than the first diameter, wherein a height of the first needle is substantially equal to a height of the first combination of three fine needles, wherein the first needle is spaced apart from the first combination of three fine needles with a predetermined distance, wherein a part of the first needle is exposed out of the body part, and another part of the first needle is disposed inside the body part, wherein a part of the first combination of three fine needles is exposed out of the body part, and another part of the first combination of three fine needles is disposed inside the body part.

14. The tattoo system of claim 13, wherein the first needle and the first combination of three fine needles are arranged on the body part in a horizontal row.

15. The tattoo system of claim 13, wherein the tattoo needle unit further comprises a second needle.

16. The tattoo system of claim 13, wherein the tattoo needle unit further comprises a second combination of three fine needles that are in contact with each other.

17. The tattoo system of claim 13, wherein the predetermined distance is 1 to 2 mm.

* * * * *